(12) United States Patent
Stauffer

(10) Patent No.: US 10,138,174 B2
(45) Date of Patent: Nov. 27, 2018

(54) MANUFACTURE OF ETHYLENE FROM ETHANOL

(71) Applicant: John E. Stauffer, Greenwich, CT (US)

(72) Inventor: John E. Stauffer, Greenwich, CT (US)

(73) Assignee: John E. Stauffer

( * ) Notice: Subject to any disclaimer, the term of this patent is extended or adjusted under 35 U.S.C. 154(b) by 0 days.

(21) Appl. No.: 15/858,471

(22) Filed: Dec. 29, 2017

(65) Prior Publication Data

US 2018/0118636 A1     May 3, 2018

Related U.S. Application Data

(63) Continuation-in-part of application No. 14/803,601, filed on Jul. 20, 2015, now abandoned.

(51) Int. Cl.

| | | |
|---|---|---|
| *C07C 1/24* | (2006.01) | |
| *C07C 1/26* | (2006.01) | |
| *C07C 11/04* | (2006.01) | |
| *C07C 1/30* | (2006.01) | |
| *B01J 21/12* | (2006.01) | |
| *B01J 19/00* | (2006.01) | |
| *B01J 21/18* | (2006.01) | |

(52) U.S. Cl.
CPC ............. *C07C 1/24* (2013.01); *B01J 19/0013* (2013.01); *B01J 21/12* (2013.01); *B01J 21/18* (2013.01); *C07C 1/30* (2013.01); *C07C 11/04* (2013.01); *B01J 2219/00051* (2013.01); *B01J 2219/00162* (2013.01); *C07C 2521/12* (2013.01); *C07C 2521/18* (2013.01)

(58) Field of Classification Search
CPC ............................. C07C 1/24; C07C 2521/12
See application file for complete search history.

(56) References Cited

U.S. PATENT DOCUMENTS

| | | | | |
|---|---|---|---|---|
| 1,834,089 A | * | 12/1931 | Johnson ................... | C07C 17/16 570/258 |
| 2,827,129 A | * | 3/1958 | Gould ....................... | C01B 7/01 423/481 |

FOREIGN PATENT DOCUMENTS

| | | | | |
|---|---|---|---|---|
| JP | 2010024185 | * | 2/2010 | ............. C07C 17/15 |

OTHER PUBLICATIONS

JP 2010-024185_English translation (Year: 2010).*

* cited by examiner

*Primary Examiner* — Youngsul Jeong
(74) *Attorney, Agent, or Firm* — Young Basile Hanlon & MacFarlane, P.C.

(57) ABSTRACT

Ethylene is produced from ethanol in a one-step process by reacting ethanol with hydrogen chloride over a catalyst composed of silica alumina catalyst in intimate admixture with activated charcoal.

10 Claims, 1 Drawing Sheet

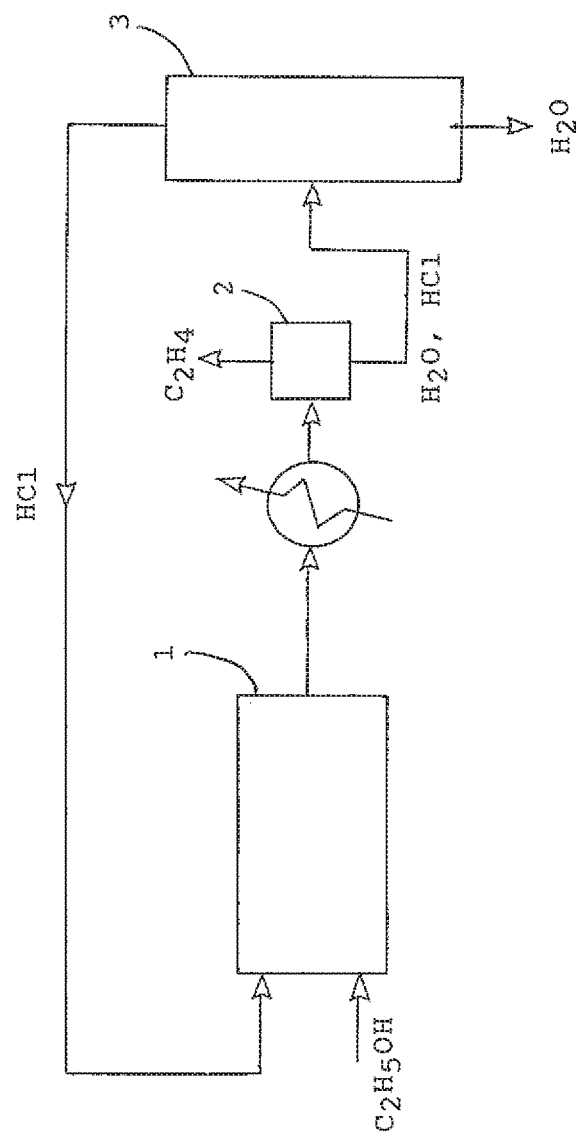

MANUFACTURE OF ETHYLENE FROM ETHANOL

CROSS-REFERENCE TO RELATED APPLICATIONS

The present application is a continuation in part of U.S. Ser. No. 14/803,601 filed Jul. 20, 2015, the contents of which are incorporated by reference herein.

FIELD OF THE INVENTION

The present invention relates to a process for manufacturing ethylene from ethanol. The process is conducted in one step by reacting ethanol in the presence of a solid catalyst, thereby dehydrating the ethanol to render ethylene and water.

BACKGROUND

There is growing interest in the manufacture of ethylene from renewable sources. This trend is motivated by concerns about global warming and the uncertainty about prices of petroleum feedstock. As a result, leading manufacturers of ethylene are turning to ethanol as a raw material. The ethanol may be supplied by the fermentation of sugar from either sugar cane or corn syrup. The chemistry for producing ethylene from ethanol is well known. It is straightforward in concept, having been the subject of much academic research. Ethylene is formed by the dehydration of ethanol in the vapor phase reaction when the alcohol is passed over a catalyst of gamma aluminum oxide at a temperature in the range of 348° to 428° C.

The commercial application of this technology, however, presents certain problems. The catalyst life is limited. Byproducts are formed, including such impurities as heavy residues, as well as light ends. Furthermore, an inherent disadvantage of the chemistry is the coproduction of ether, which must be recovered and recycled in the process.

For these and other reasons, there is an incentive to develop new technology for the production of ethylene from ethanol. Thus, it is a goal of the present disclosure to provide a process that is efficient, robust and versatile in its use. These and other advantages, features, and characteristics of the process of the present disclosure will become apparent from the following description and the FIGURE that is included.

SUMMARY

A process is provided for the synthesis of ethylene from ethanol in a one-step process. In the process as disclosed, pure ethanol vapor and hydrogen chloride are passed over a solid catalyst to dehydrate the ethanol to form ethylene In the overall reaction, hydrogen chloride reacts with ethanol to form water and ethyl chloride. The latter in turn is cracked to form ethylene and release hydrogen chloride. In effect, the hydrogen chloride acts simply as a catalyst, passing through the process unchanged.

Purified product is produced by separating water and hydrogen chloride from the ethylene. The hydrogen chloride is recycled in order to provide a self-contained process.

BRIEF DESCRIPTION OF THE DRAWING

The single figure is a block diagram showing the principal features of the process. Intermediate and product streams are indicated on the flow sheet.

DETAILED DESCRIPTION

The present invention is predicated on the unexpected discovery that two chemical reactions that can be identified in the process disclosed herein take place simultaneously and occur in intimate contact in a single catalytic reaction chamber to produce ethylene. These two reactions are shown by the following equations:

$$C_2H_5OH + HCl \rightarrow C_2H_5Cl + H_2O \quad\quad 1.$$

$$C_2H_5Cl \rightarrow C_2H_4 + HCl \quad\quad 2.$$

The net result of these reactions is as follows:

$$C_2H_5OH \rightarrow C_2H_4 + H_2O \quad\quad 3.$$

In the reaction scheme shown above, the ethyl chloride produced in the first reaction is consumed in the second reaction. Similarly, the requirement of hydrogen chloride for the first reaction is supplied by the second reaction. Depending on the physical design of the reactor and the feed streams, the quantity of hydrogen chloride that is supplied to the reaction chamber can be minimal.

In the process as disclosed, a feed stock consisting essentially of ethanol is introduced into contact with a catalytic material in a suitable reaction vessel. The ethanol in the feed stock can be present in pure form or near pure form. In certain embodiments, the ethanol feed stock will be composed of between 97% and 100% ethanol.

The ethanol feed stock is introduced into contact with a catalytic material consisting essentially of activated carbon material and silica alumina in intimate admixture. "Intimate admixture" as the term is applied in this disclosure is defined to include configurations in which the feed stock and transient reaction intermediates are able to contact both catalytic materials while resident in the reaction chamber. In certain embodiments, some or all of the catalytic material can be and admixture of high surface area activated carbon material and high surface area. The catalytic materials can be present in the reactor in any suitable form to promote contact with the feed stock and transitory intermediates. Non-limiting examples of such configurations include at least one of the following: pellets, spheres, granules, extruded pellets, rings, spoked wheels and the like. Where desired or required, it is contemplated that at least portion of the silica alumina can be present as a support for activated carbon material.

The activated carbon material employed in the catalytic bed can be one or more of the following, alone or in combination: activated charcoal, activated coke, activated coal. Suitable activated carbon materials can have a surface area in excess of 1000 m² per gram with surface areas between 4000 and 10,000 m² per gram in certain applications. In certain embodiments, the activated carbon catalytic material will be activated charcoal or activated biochar. Suitable activated charcoal materials may have a graphite like morphology had random pore structure greater than 1000 m² per gram. Where desired or required, the activated biochar and/or activated charcoal can be supported by on a suitable catalytic support, non-limiting examples include ruthenium, alumina and the like.

The silica alumina material employed as catalytic material can be a suitable commercially available catalytic grade material. Without being bound to any theory, it is believed that suitable catalytic material can include, in whole or in part, materials such as those commercially available under CAS number 1335-30-4. In certain embodiments, it is contemplated that Grade 135 can be employed.

In some embodiments, the activated carbon material can be present as a particulate material in intimate admixture with particulate silica alumina at a carbon-to silica ratios between 1 to 5 and 5 to 1, weight to weight. In certain embodiments, it is contemplated that the ratio of activated carbon material to silica alumina will be between 1:3 and 3:1, while in some specific embodiments.

In the process disclosed, the catalytic material is present in a single reaction vessel and, more particularly, is a reaction bed. Heretofore, it was believed multiple catalytic beds and/or reactors would be necessary to efficiently and effectively produce ethylene from and ethanol feed stock. In contrast, the present invention is predicated on the unexpected discovery that Reactions 1 and 2, chlorination of ethanol to produce ethylene chloride and its subsequent dechlorination to form ethane and hydrochloric acid can be accomplished efficiently and effectively in a single catalytic bed which supports both reactions. The catalyzed reaction proceeds to completion with the formation of little to no byproducts.

The literature extensively discusses the chemistry shown by equation 1. Various alkyl chlorides can be made from the corresponding alcohols making use of hydrogen chloride as a direct chlorinating agent in organic synthesis. Thus, methyl, ethyl, and propyl chlorides can be made by a vapor phase reaction of the given alcohol. This chlorination reaction is carried out at a temperature of 200° to 300° C. over an alumina silica catalyst mass containing 0.01 to 1 percent $Na_2O$. This reaction can proceed to various degrees of completion. Thus, it is possible that the reaction, proceeding in the presence of an alumina silica mass containing 0.01 to 1 percent $Na_2O$, can yield ethyl, methyl and/or propyl chlorides and various by-products.

It has been found, quite unexpectedly that pure ethanol in vapor form can be reacted in the presence of hydrogen chloride and a catalyst that consists essentially of alumina silica and activated charcoal in intimate mixture can support a reaction that produces ethyl chloride with little or no by-products.

Supplementing these results, experimental data can be obtained for the reaction given by equation 2 supported by the silica alumina catalytic material in intimate mixture with activated carbon. Various other individual catalysts for this reaction, though numerous, do not efficiently support the proposed reaction. While activated charcoal as an individual catalyst shows some activity, it was found to be less effective than other catalysts such as zinc chloride or alumina silica. Zinc chloride has the disadvantage of its volatility so that steps need to be taken to maintain its activity. Thus, it was unexpected that the use of a catalytic material that includes both silica alumina and activated charcoal would produce the augmented reaction results that were observed.

Using silica alumina and activated carbon material such as activated charcoal as a cracking catalyst, the reaction as shown by equation 2 will have be endothermic. Typically, such as reaction will require a temperature in the range of 325° to 375° C. to proceed. Given the endothermicity of the reaction shown in Equation 2 it is expected that heat must be supplied to the reactor. Under these conditions, the results are near perfect.

It has been found, quite unexpectedly, that the chemistry for the chlorination of ethanol with the science for cracking ethyl chloride, a one-step operation can be obtained. In this unified process, the catalyst of choice is an intimate mixture of silica alumina and activated carbon such as activated charcoal which has been found to be active for both chlorination and cracking. This catalytic material composition is effective over a wide spectrum of temperatures from 300° C. to 400° C., with ranges from 300° to 325° C., 325° C. to 350° C., 350° to 375° C., 375° C. to 400° C. in certain embodiments without sacrificing efficiency.

The reaction is carried out at a pressure in the range of 1 to 10 atmospheres (gauge), with ranges between 1 and 3 atmospheres (gauge) in certain embodiments.

The reaction product that results from the process as disclosed, comprises contacting a pure ethanol feed stream with a catalytic material that comprises silica alumina and activated charcoal in intimate admixture in a reactor to produce a reaction effluent that consists of water and ethylene.

The advantages of the present invention are best illustrated by referring to the single figure Pure ethanol and hydrogen chloride are fed to reactor 1, which typically may consist of a shell and tube design at a reaction temperature between 300° C. and 400° C. The resulting effluent consists essentially of ethylene and water. The resulting effluent is then cooled in a heat exchanger and then passed to phase separator 2 where the ethylene product is recovered. Hydrochloric acid is sent to distillation column 3 to recover hydrogen chloride for recycle to reactor 1.

EXAMPLE

In a laboratory experiment, ethyl chloride is cracked over a catalyst material that consists of commercial silica alumina catalyst material in intimate contact with activated charcoal at 350° C. to give a near quantitative yield of ethylene. The silica alumina catalyst has a composition of 12.4 weight percent $Al_2O_3$ and 87.3 weight percent $SiO_2$ and is in intimate combination with activated charcoal in 50-50 mixture. The catalytic material has a surface area of 300 $m^2$ per gm. The pellet density is 0.99 kg per liter and porosity equaled 57 volume percent. The resulting reaction effluent consists of ethylene and water. No by-products are noted or detected. No loss of catalyst activity is noted during the experiment.

SUMMARY

A process is provided for the synthesis of ethylene from ethanol in a one-step process. In the process as disclosed, pure ethanol vapor and hydrogen chloride are passed over a solid catalyst to dehydrate the ethanol to form ethylene.

In the overall reaction, hydrogen chloride reacts with ethanol to form water and ethyl chloride. The latter in turn is cracked to form ethylene and release hydrogen chloride. In effect, the hydrogen chloride acts simply as a catalyst, passing through the process unchanged.

Purified product is produced by separating water and hydrogen chloride from the ethylene. The hydrogen chloride is recycled in order to provide a self-contained process.

What is claimed is:
1. A process for the synthesis of ethylene from substantially pure ethanol including the steps of carrying out two simultaneous reactions in the presence of a solid catalyst wherein the first reaction is
   (a) $C_2H_5OH + HCl \rightarrow C_2H_5Cl + H_2O$, and the second reaction is
   (b) $C_2H_5Cl \rightarrow C_2H_4 + HCl$
   (c) wherein the HCl produced in reaction (b) is consumed in reaction (a) and the HCl for reaction (a) is supplied by reaction (b), and wherein said two simultaneous reactions take place in a reaction vessel containing the solid catalyst of an intimate admixture of activated carbon and silica alumina.

2. The process of claim 1 wherein the substantially pure ethanol is present as a vapor and wherein the ethanol in the vapor is reacted with hydrogen chloride in the present of the solid catalyst.

3. The process according to claim 1 in which the reaction between the substantially pure ethanol and the hydrogen chloride is conducted at a temperature range of 300° C. to 400° C. and at a pressure between 1 and 10 atmospheres (gauge).

4. The process according to claim 1 in which the reaction between the substantially pure ethanol and the hydrogen chloride is conducted at a temperature range of 350° C. to 400° C. and at a pressure between 1 and 3 atmospheres (gauge).

5. The process according to claim 1 in which the silica alumina and the activated carbon are present in the solid catalyst in a silica alumina to activated carbon weight ratio between 5 to 1 and 1 to 5.

6. The process according to claim 1 in which the silica alumina and the activated carbon are present in the solid catalyst in a silica alumina to activated carbon weight ratio between 3 to 1 and 1 to 3.

7. The process according to claim 1 in which the silica alumina and the activated carbon are present in the solid catalyst in a silica alumina to activated carbon weight ratio between 2 to 1 and 1 to 2.

8. A process for the manufacture of ethylene as an end product comprising the steps of:
   reacting substantially pure vaporous ethanol over a solid catalyst of pure silica alumina in intimate admixture with activated carbon at a temperature between 300° C. and 400° C. and a pressure between 1 and 10 atmospheres (gauge) in the presence of hydrogen chloride; and
   producing a reaction effluent comprising ethylene.

9. The process of claim 8 further comprising steps of collecting the reaction effluent consisting essentially of water and ethylene and separating the water from the reaction effluent to produce dried ethylene.

10. The process of claim 9 wherein the temperature is between 350° C. and 400° C.

\* \* \* \* \*